(12) United States Patent
Donhowe et al.

(10) Patent No.: US 11,957,424 B2
(45) Date of Patent: Apr. 16, 2024

(54) SYSTEMS AND METHODS FOR PLANNING MULTIPLE INTERVENTIONAL PROCEDURES

(71) Applicant: INTUITIVE SURGICAL OPERATIONS, INC., Sunnyvale, CA (US)

(72) Inventors: Caitlin Q. Donhowe, Mountain View, CA (US); Tao Zhao, Sunnyvale, CA (US); Federico Barbagli, San Francisco, CA (US); Vincent Duindam, San Francisco, CA (US); Timothy D. Soper, San Jose, CA (US)

(73) Assignee: INTUITIVE SURGICAL OPERATIONS, INC., Sunnyvale, CA (US)

( * ) Notice: Subject to any disclaimer, the term of this patent is extended or adjusted under 35 U.S.C. 154(b) by 0 days.

(21) Appl. No.: 17/720,151

(22) Filed: Apr. 13, 2022

(65) Prior Publication Data
US 2022/0233265 A1    Jul. 28, 2022

Related U.S. Application Data

(63) Continuation of application No. 15/329,899, filed as application No. PCT/US2015/040994 on Jul. 17, 2015, now Pat. No. 11,351,000.
(Continued)

(51) Int. Cl.
*A61B 34/35* (2016.01)
*A61B 17/00* (2006.01)
(Continued)

(52) U.S. Cl.
CPC .............. *A61B 34/35* (2016.02); *A61B 34/20* (2016.02); *A61B 34/25* (2016.02); *A61B 34/30* (2016.02);
(Continued)

(58) Field of Classification Search
None
See application file for complete search history.

(56) References Cited

U.S. PATENT DOCUMENTS

| 4,984,575 A | 1/1991 | Uchiyama et al. |
| 6,380,732 B1 | 4/2002 | Gilboa |
| (Continued) | | |

FOREIGN PATENT DOCUMENTS

| CN | 102640014 B | 7/2014 |
| JP | 2005131319 A | 5/2005 |
| (Continued) | | |

OTHER PUBLICATIONS

Extended European Search Report for Application No. EP15827886.1, dated Feb. 13, 2018, 8 pages.
(Continued)

*Primary Examiner* — Catherine M Voorhees
*Assistant Examiner* — Elizabeth K So
(74) *Attorney, Agent, or Firm* — Haynes & Boone, LLP

(57) ABSTRACT

A system includes an interventional instrument and a control system. The control system is configured to: generate a graphical user interface (GUI) including an image of a target region for deploying the interventional instrument, wherein the target region includes a plurality of target points and is determined by a probabilistic collection of the plurality of target points, wherein a size of the target region is based at least in part on a location of a target structure within a patient anatomy; responsive to an engagement of the interventional instrument with tissue in the target region, update the GUI to include an engagement location marker; and responsive to the engagement of the interventional instrument, update the GUI to include an image of a revised target region.

20 Claims, 9 Drawing Sheets

Related U.S. Application Data

(60) Provisional application No. 62/029,942, filed on Jul. 28, 2014.

(51) Int. Cl.

| | | |
|---|---|---|
| *A61B 34/00* | (2016.01) | |
| *A61B 34/10* | (2016.01) | |
| *A61B 34/20* | (2016.01) | |
| *A61B 34/30* | (2016.01) | |
| *A61B 34/37* | (2016.01) | |
| *A61B 90/00* | (2016.01) | |
| *A61B 90/50* | (2016.01) | |

(52) U.S. Cl.
CPC .............. *A61B 34/37* (2016.02); *A61B 34/74* (2016.02); *A61B 34/76* (2016.02); *A61B 90/50* (2016.02); *A61B 2017/00694* (2013.01); *A61B 2017/00809* (2013.01); *A61B 2034/105* (2016.02); *A61B 2034/107* (2016.02); *A61B 2034/2051* (2016.02); *A61B 2034/2057* (2016.02); *A61B 2034/2061* (2016.02); *A61B 2034/301* (2016.02); *A61B 2034/306* (2016.02); *A61B 34/71* (2016.02); *A61B 2034/741* (2016.02); *A61B 2034/742* (2016.02); *A61B 2090/3614* (2016.02); *A61B 2090/371* (2016.02)

(56) References Cited

U.S. PATENT DOCUMENTS

| | | | |
|---|---|---|---|
| 6,389,187 | B1 | 5/2002 | Greenaway et al. |
| 7,316,681 | B2 | 1/2008 | Madhani et al. |
| 7,318,805 | B2 | 1/2008 | Schweikard et al. |
| 7,772,541 | B2 | 8/2010 | Froggatt et al. |
| 7,930,065 | B2 | 4/2011 | Larkin et al. |
| 8,900,131 | B2 | 12/2014 | Chopra et al. |
| 9,259,274 | B2 | 2/2016 | Prisco |
| 9,452,276 | B2 | 9/2016 | Duindam et al. |
| 11,351,000 | B2 * | 6/2022 | Donhowe .............. A61B 34/37 |
| 2004/0152971 | A1 | 8/2004 | Kukuk |
| 2006/0013523 | A1 | 1/2006 | Childlers et al. |
| 2008/0161687 | A1 | 7/2008 | Suri et al. |
| 2009/0118640 | A1 | 5/2009 | Miller et al. |
| 2009/0156895 | A1 | 6/2009 | Higgins et al. |
| 2011/0295108 | A1 * | 12/2011 | Cox ........................ A61B 5/339 |
| | | | 600/424 |
| 2012/0143029 | A1 | 6/2012 | Silverstein et al. |
| 2013/0090554 | A1 | 4/2013 | Zvuloni et al. |
| 2013/0303892 | A1 | 11/2013 | Zhao et al. |
| 2014/0187949 | A1 | 7/2014 | Zhao et al. |
| 2015/0320492 | A1 | 11/2015 | Ben-Haim |
| 2017/0265952 | A1 | 9/2017 | Donhowe et al. |
| 2020/0214664 | A1 | 7/2020 | Zhao et al. |

FOREIGN PATENT DOCUMENTS

| | | |
|---|---|---|
| JP | 2008005923 A | 1/2008 |
| JP | 2013519486 A | 5/2013 |
| JP | 2013198722 A | 10/2013 |
| WO | WO-2014106253 A1 | 7/2014 |

OTHER PUBLICATIONS

International Preliminary Report on Patentability for Application No. PCT/US2015/040994, dated Feb. 9, 2017, 15 pages.
International Search Report and Written Opinion for Application No. PCT/US15/040994, dated Oct. 20, 2015, 18 pages.
Vertut, J, and Coiffet, P., "Robot Technology: Teleoperation and Robotics Evolution and Development," English translation, Prentice-Hall, Inc., Inglewood Cliffs, NJ, USA 1986, vol. 3A, 332 pages.

\* cited by examiner

SYSTEMS AND METHODS FOR PLANNING MULTIPLE INTERVENTIONAL PROCEDURES

RELATED APPLICATIONS

This patent application is a continuation of U.S. patent application Ser. No. 15/329,899, filed Jan. 27, 2017, (patented as U.S. Pat. No. 11,351,000) which is the U.S. national phase of International Application No. PCT/US2015/040994, filed Jul. 17, 2015, which designated the U.S. and claims priority to and the benefit of the filing date of U.S. Provisional Patent Application 62/029,942, entitled "SYSTEMS AND METHODS FOR PLANNING MULTIPLE INTERVENTIONAL PROCEDURES," filed Jul. 28, 2014, all of which are incorporated by reference herein in their entirety.

FIELD

The present disclosure is directed to systems and methods for navigating a patient anatomy to conduct a minimally invasive procedure, and more particularly to systems and methods for planning a procedure for multiple deployments of an interventional instrument.

BACKGROUND

Minimally invasive medical techniques are intended to reduce the amount of tissue that is damaged during interventional procedures, thereby reducing patient recovery time, discomfort, and deleterious side effects. Such minimally invasive techniques may be performed through natural orifices in a patient anatomy or through one or more surgical incisions. Through these natural orifices or incisions clinicians may insert interventional instruments (including surgical, diagnostic, therapeutic, or biopsy instruments) to reach a target tissue location. To reach the target tissue location, a minimally invasive interventional instrument may navigate natural or surgically created passageways in anatomical systems such as the lungs, the colon, the intestines, the kidneys, the heart, the circulatory system, or the like. To assist the clinician in navigating the instrument through the passageways, models of the passageway are prepared using pre-operative or inter-operative imaging. Current systems for deploying an interventional instrument identify an instrument deployment location as the point within the modeled passageways closest to a target tissue location. The target tissue location may be inaccurate for a variety of reasons. For example, the locations of anatomic structures are different in a moving patient than in a static pre-operative image-based model. Position sensor errors and the accuracy of registration techniques may also contribute to inaccuracies in determining the target tissue location. Improved systems and methods are needed for conducting a minimally invasive procedure to increase the likelihood of accessing the target tissue location.

SUMMARY

The embodiments of the invention are summarized by the claims that follow the description.

In one embodiment, a method of deploying an interventional instrument comprises identifying a target structure in an anatomic frame of reference. The method further comprises determining a target region in the anatomic frame of reference with respect to a current position of the interventional instrument and recording a first engagement location of the interventional instrument within the target region.

In another embodiment, a method for performing an interventional procedure comprises generating a graphical user interface (GUI) including an image of a target region for deploying an interventional instrument. Responsive to a first engagement of the interventional instrument, the GUI is updated to include a first engagement location marker. Responsive to the first engagement of the interventional instrument, the GUI is updated to include an image of a first revised target region.

In another embodiment, a method for planning multiple interventional procedures comprises identifying a target structure in an anatomic frame and determining a target region in the anatomic frame. The target structure is located within the target region. The method further comprises identifying a first engagement location within the target region for deploying an interventional instrument and identifying a second engagement location for deploying the interventional instrument.

In another embodiment, a system comprises an interventional instrument including a catheter and a tool deployable from the catheter. The system also includes a control system configured to identify a target structure in an anatomic frame of reference and determine a target region in the anatomic frame of reference with respect to a current location of the interventional instrument. The target structure is located within the target region. The control system is further configured to record a first engagement location of the interventional instrument within the target region and record a second engagement location of the interventional instrument within the target region.

BRIEF DESCRIPTIONS OF THE DRAWINGS

Aspects of the present disclosure are best understood from the following detailed description when read with the accompanying figures. It is emphasized that, in accordance with the standard practice in the industry, various features are not drawn to scale. In fact, the dimensions of the various features may be arbitrarily increased or reduced for clarity of discussion. In addition, the present disclosure may repeat reference numerals and/or letters in the various examples. This repetition is for the purpose of simplicity and clarity and does not in itself dictate a relationship between the various embodiments and/or configurations discussed.

DETAILED DESCRIPTION

In the following detailed description of the aspects of the invention, numerous specific details are set forth in order to provide a thorough understanding of the disclosed embodiments. However, it will be obvious to one skilled in the art that the embodiments of this disclosure may be practiced without these specific details. In other instances well known methods, procedures, components, and circuits have not been described in detail so as not to unnecessarily obscure aspects of the embodiments of the invention. And, to avoid needless descriptive repetition, one or more components or actions described in accordance with one illustrative embodiment can be used or omitted as applicable from other illustrative embodiments.

The embodiments below will describe various instruments and portions of instruments in terms of their state in three-dimensional space. As used herein, the term "position" refers to the location of an object or a portion of an object in a three-dimensional space (e.g., three degrees of translational freedom along Cartesian X, Y, Z coordinates). As used herein, the term "orientation" refers to the rotational placement of an object or a portion of an object (three degrees of rotational freedom—e.g., roll, pitch, and yaw). As used herein, the term "pose" refers to the position of an object or a portion of an object in at least one degree of translational freedom and to the orientation of that object or portion of the object in at least one degree of rotational freedom (up to six total degrees of freedom). As used herein, the term "shape" refers to a set of poses, positions, or orientations measured along an object.

Figure 1:
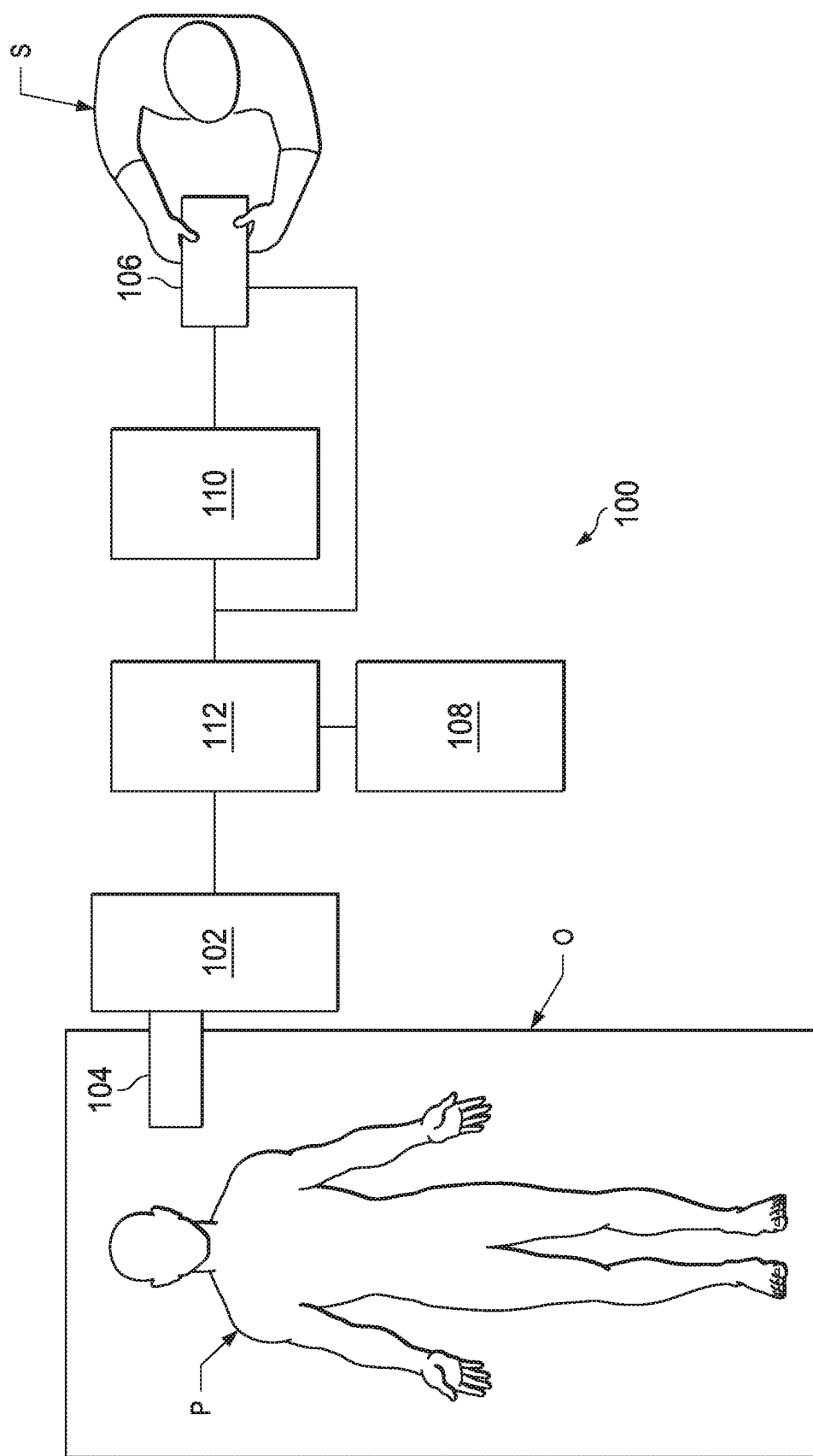
FIG. 1 is a teleoperated interventional system, in accordance with embodiments of the present disclosure.

Referring to FIG. 1 of the drawings, a teleoperated interventional system for use in, for example, surgical, diagnostic, therapeutic, or biopsy procedures, is generally indicated by the reference numeral 100. As shown in FIG. 1, the teleoperated system 100 generally includes an interventional manipulator assembly 102 for operating an interventional instrument 104 in performing various procedures on the patient P. The assembly 102 is mounted to or near an operating table O. A master assembly 106 allows the clinician or surgeon S to view the interventional site and to control the slave manipulator assembly 102.

The master assembly 106 may be located at a surgeon's console which is usually located in the same room as operating table O. However, it should be understood that the surgeon S can be located in a different room or a completely different building from the patient P. Master assembly 106 generally includes one or more control devices for controlling the manipulator assemblies 102. The control devices may include any number of a variety of input devices, such as joysticks, trackballs, data gloves, trigger-guns, hand-operated controllers, voice recognition devices, body motion or presence sensors, or the like. In some embodiments, the control devices will be provided with the same degrees of freedom as the associated interventional instruments 104 to provide the surgeon with telepresence, or the perception that the control devices are integral with the instruments 104 so that the surgeon has a strong sense of directly controlling instruments 104. In other embodiments, the control devices may have more or fewer degrees of freedom than the associated interventional instruments 104 and still provide the surgeon with telepresence. In some embodiments, the control devices are manual input devices which move with six degrees of freedom, and which may also include an actuatable handle for actuating instruments (for example, for closing grasping jaws, applying an electrical potential to an electrode, delivering a medicinal treatment, or the like).

The teleoperational assembly 102 supports the medical instrument system 104 and may include a kinematic structure of one or more non-servo controlled links (e.g., one or more links that may be manually positioned and locked in place, generally referred to as a set-up structure) and a teleoperational manipulator. The teleoperational assembly 102 includes plurality of actuators or motors that drive inputs on the medical instrument system 104 in response to commands from the control system (e.g., a control system 112). The motors include drive systems that when coupled to the medical instrument system 104 may advance the medical instrument into a naturally or surgically created anatomical orifice. Other motorized drive systems may move the distal end of the medical instrument in multiple degrees of freedom, which may include three degrees of linear motion (e.g., linear motion along the X, Y, Z Cartesian axes) and in three degrees of rotational motion (e.g., rotation about the X, Y, Z Cartesian axes). Additionally, the motors can be used to actuate an articulable end effector of the instrument for grasping tissue in the jaws of a biopsy device or the like.

The teleoperational medical system 100 also includes a sensor system 108 with one or more sub-systems for receiving information about the instruments of the teleoperational assembly. Such sub-systems may include a position sensor system (e.g., an electromagnetic (EM) sensor system); a shape sensor system for determining the position, orientation, speed, velocity, pose, and/or shape of the catheter tip and/or of one or more segments along a flexible body of instrument system 104; and/or a visualization system for capturing images from the distal end of the catheter system.

The visualization system (e.g., visualization system 231 of FIG. 2) may include a viewing scope assembly (described in greater detail below) such that a concurrent or real-time image of the surgical site is provided to clinician or surgeon S. The concurrent image may be, for example, a two or three dimensional image captured by an endoscope positioned within the surgical site. In this embodiment, the visualization system includes endoscopic components that may be integrally or removably coupled to the medical instrument 104. However in alternative embodiments, a separate endoscope, attached to a separate manipulator assembly may be used with the medical instrument to image the surgical site. The visualization system may be implemented as hardware, firmware, software or a combination thereof which interact with or are otherwise executed by one or more computer processors, which may include the processors of a control system 112 (described below).

The teleoperational medical system 100 also includes a display system 110 for displaying an image or representation of the surgical site and medical instrument system(s) 104 generated by sub-systems of the sensor system 108. The display 110 and the operator input system 106 may be oriented so the operator can control the medical instrument system 104 and the operator input system 106 with the perception of telepresence.

The display system 110 may also display an image of the surgical site and medical instruments captured by the visualization system. The display 110 and the control devices may be oriented such that the relative positions of the imaging device in the scope assembly and the medical instruments are similar to the relative positions of the surgeon's eyes and hands so the operator can manipulate the medical instrument 104 and the hand control as if viewing the workspace in substantially true presence. By true presence, it is meant that the presentation of an image is a true perspective image simulating the viewpoint of an operator that is physically manipulating the instrument 104.

Alternatively or additionally, the display 110 may present images of the surgical site recorded and/or modeled preoperatively using data from imaging technology such as, computed tomography (CT), magnetic resonance imaging (MRI), fluoroscopy, thermography, ultrasound, optical coherence tomography (OCT), thermal imaging, impedance imaging, laser imaging, or nanotube X-ray imaging. The presented preoperative images may include two-dimensional, three-dimensional, or four-dimensional images. The presented preoperative or intra-operative images may include two-dimensional, three-dimensional, or four-dimensional (including e.g., time based or velocity based information) images and associated image data sets for reproducing the images.

In some embodiments, the display 110 may display a virtual navigational image in which the actual location of the medical instrument 104 is registered (i.e., dynamically referenced) with preoperative or concurrent images to present the clinician or surgeon S with a virtual image of the internal surgical site from the viewpoint of the location of the tip of the instrument 104. An image of the tip of the instrument 104 or other graphical or alphanumeric indicators may be superimposed on the virtual image to assist the surgeon controlling the medical instrument. Alternatively, the instrument 104 may not be visible in the virtual image.

In other embodiments, the display 110 may display a virtual navigational image in which the actual location of the medical instrument is registered with preoperative or concurrent images to present the clinician or surgeon S with a virtual image of medical instrument within the surgical site from an external viewpoint. An image of a portion of the medical instrument or other graphical or alphanumeric indicators may be superimposed on the virtual image to assist the surgeon controlling the instrument 104.

The teleoperational medical system 100 also includes a control system 112. The control system 112 includes at least one memory and at least one processor (not shown), and typically a plurality of processors, for effecting control between the medical instrument system 104, the operator input system 106, the sensor system 108, and the display system 110. The control system 112 also includes programmed instructions (e.g., a computer-readable medium storing the instructions) to implement some or all of the methods described in accordance with aspects disclosed herein. While control system 112 is shown as a single block in the simplified schematic of FIG. 1, the system may include two or more data processing circuits with one portion of the processing optionally being performed on or adjacent the teleoperational assembly 102, another portion of the processing being performed at the operator input system 106, and the like. Any of a wide variety of centralized or distributed data processing architectures may be employed. Similarly, the programmed instructions may be implemented as a number of separate programs or subroutines, or they may be integrated into a number of other aspects of the teleoperational systems described herein. In one embodiment, control system 112 supports wireless communication protocols such as Bluetooth, IrDA, HomeRF, IEEE 802.11, DECT, and Wireless Telemetry.

In some embodiments, control system 112 may include one or more servo controllers that receive force and/or torque feedback from the medical instrument system 104. Responsive to the feedback, the servo controllers transmit signals to the operator input system 106. The servo controller(s) may also transmit signals instructing teleoperational assembly 102 to move the medical instrument system(s) 104 which extend into an internal surgical site within the patient body via openings in the body. Any suitable conventional or specialized servo controller may be used. A servo controller may be separate from, or integrated with, teleoperational assembly 102. In some embodiments, the servo controller and teleoperational assembly are provided as part of a teleoperational arm cart positioned adjacent to the patient's body.

The control system 112 may further include a virtual visualization system to provide navigation assistance to the medical instrument system(s) 104. Virtual navigation using the virtual visualization system is based upon reference to an acquired dataset associated with the three dimensional structure of the anatomical passageways. More specifically, the virtual visualization system processes images of the surgical site imaged using imaging technology such as computerized tomography (CT), magnetic resonance imaging (MRI), fluoroscopy, thermography, ultrasound, optical coherence tomography (OCT), thermal imaging, impedance imaging, laser imaging, nanotube X-ray imaging, or the like. Software alone or in combination with manual input is used to convert the recorded images into segmented two dimensional or three dimensional composite representation of a partial or an entire anatomical organ or anatomical region. An image data set is associated with the composite representation. The composite representation and the image data set describe the various locations and shapes of the passageways and their connectivity. The images used to generate the composite representation may be recorded preoperatively or intra-operatively during a clinical procedure. In an alternative embodiment, a virtual visualization system may use standard representations (i.e., not patient specific) or hybrids of a standard representation and patient specific data. The composite representation and any virtual images generated by the composite representation may represent the static posture of a deformable anatomic region during one or more phases of motion (e.g., during an inspiration/expiration cycle of a lung).

During a virtual navigation procedure, the sensor system 108 may be used to compute an approximate location of the instrument with respect to the patient anatomy. The location can be used to produce both macro-level tracking images of the patient anatomy and virtual internal images of the patient anatomy. Various systems for using fiber optic sensors to register and display a medical implement together with preoperatively recorded surgical images, such as those from a virtual visualization system, are known. For example U.S. patent application Ser. No. 13/107,562 (filed May 13, 2011) (disclosing "Medical System Providing Dynamic Registration of a Model of an Anatomical Structure for Image-Guided Surgery") (patented as U.S. Pat. No. 8,900,131) which is incorporated by reference herein in its entirety, discloses one such system.

The teleoperational medical system 100 may further include optional operation and support systems (not shown) such as illumination systems, steering control systems, irrigation systems, and/or suction systems. In alternative embodiments, the teleoperational system may include more than one teleoperational assembly and/or more than one operator input system. The exact number of manipulator assemblies will depend on the surgical procedure and the space constraints within the operating room, among other factors. The operator input systems may be collocated, or they may be positioned in separate locations. Multiple operator input systems allow more than one operator to control one or more manipulator assemblies in various combinations.

Figure 2:
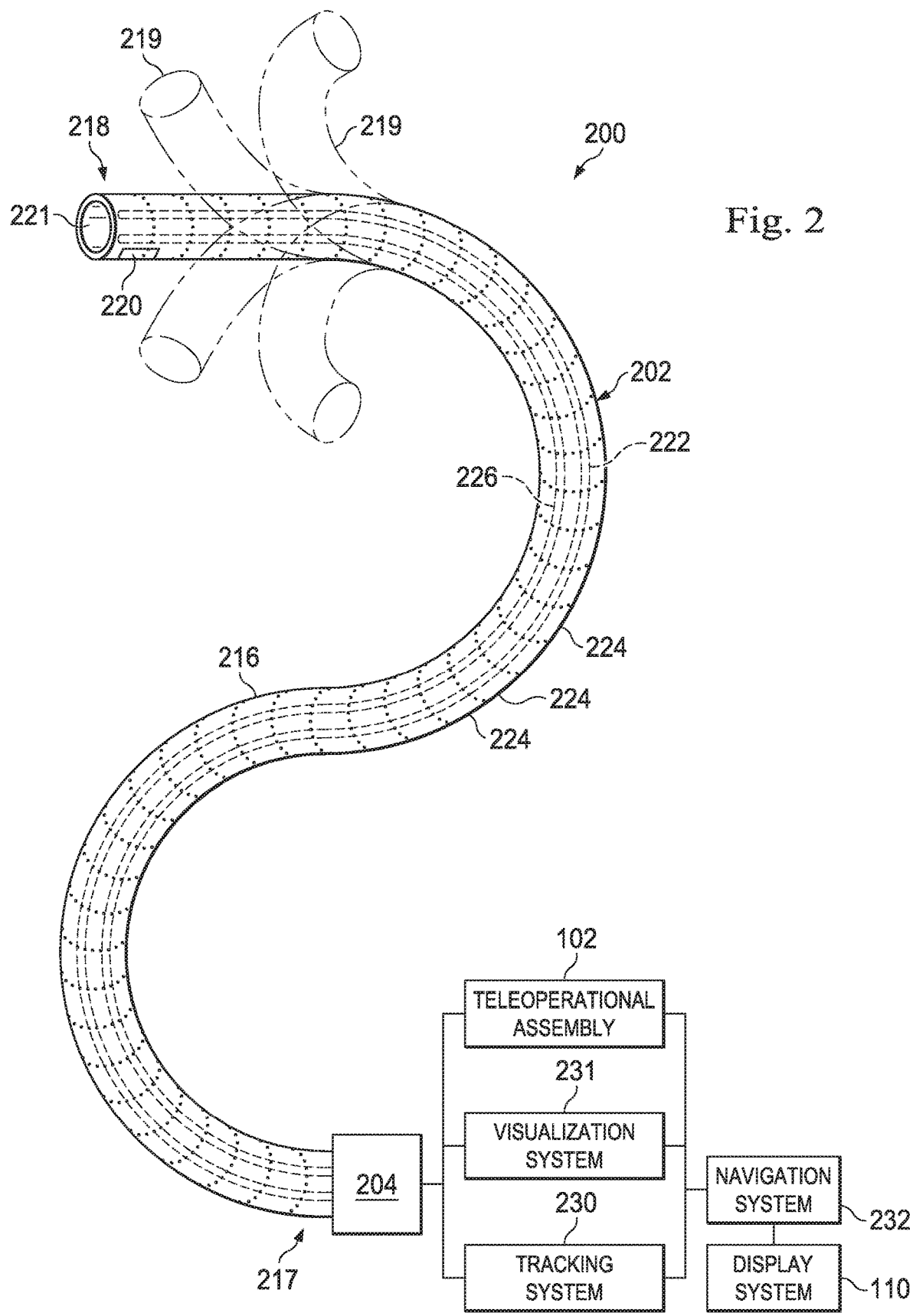
FIG. 2 illustrates an interventional instrument system utilizing aspects of the present disclosure.

FIG. 2 illustrates a medical instrument system 200, which may be used as the medical instrument system 104 of teleoperational medical system 100. Alternatively, the medical instrument system 200 may be used for non-teleoperational exploratory procedures or in procedures involving traditional manually operated medical instruments, such as endoscopy.

The instrument system 200 includes a catheter system 202 coupled to an instrument body 204. The catheter system 202 includes an elongated flexible catheter body 216 having a proximal end 217 and a distal end or tip portion 218. In one embodiment, the flexible body 216 has an approximately 3 mm outer diameter. Other flexible body outer diameters may be larger or smaller. The catheter system 202 may optionally include a shape sensor 222 for determining the position, orientation, speed, velocity, pose, and/or shape of the catheter tip at distal end 218 and/or of one or more segments 224 along the body 216. The entire length of the body 216, between the distal end 218 and the proximal end 217, may be effectively divided into the segments 224. If the instrument system 200 is a medical instrument system 104 of a teleoperational medical system 100, the shape sensor 222 may be a component of the sensor system 108. If the instrument system 200 is manually operated or otherwise used for non-teleoperational procedures, the shape sensor 222 may be coupled to a tracking system 230 that interrogates the shape sensor and processes the received shape data.

The shape sensor 222 may include an optical fiber aligned with the flexible catheter body 216 (e.g., provided within an interior channel (not shown) or mounted externally). In one embodiment, the optical fiber has a diameter of approximately 200 μm. In other embodiments, the dimensions may be larger or smaller. The optical fiber of the shape sensor system 222 forms a fiber optic bend sensor for determining the shape of the catheter system 202. In one alternative, optical fibers including Fiber Bragg Gratings (FBGs) are used to provide strain measurements in structures in one or more dimensions. Various systems and methods for monitoring the shape and relative position of an optical fiber in three dimensions are described in U.S. patent application Ser. No. 11/180,389 (filed Jul. 13, 2005) (disclosing "Fiber optic position and shape sensing device and method relating thereto") (published as U.S. Pat. App. Pub. No. 2006/0013523—abandoned); U.S. patent application Ser. No. 12/047,056 (filed on Jul. 16, 2004) (disclosing "Fiber-optic shape and relative position sensing") (patented as U.S. Pat. No. 7,772,541); and U.S. Pat. No. 6,389,187 (filed on Jun. 17, 1998) (disclosing "Optical Fibre Bend Sensor"), which are all incorporated by reference herein in their entireties. Sensors in alternative embodiments may employ other suitable strain sensing techniques, such as Rayleigh scattering, Raman scattering, Brillouin scattering, and Fluorescence scattering. In other alternative embodiments, the shape of the catheter may be determined using other techniques. For example, the history of the catheter's distal tip pose can be used to reconstruct the shape of the device over the interval of time. As another example, historical pose, position, or orientation data may be stored for a known point of an instrument system along a cycle of alternating motion, such as breathing. This stored data may be used to develop shape information about the catheter. Alternatively, a series of positional sensors, such as EM sensors, positioned along the catheter can be used for shape sensing. Alternatively, a history of data from positional sensor, such as an EM sensor, on the instrument system during a procedure may be used to represent the shape of the instrument, particularly if an anatomical passageway is generally static. Alternatively, a wireless device with position or orientation controlled by an external magnetic field may be used for shape sensing. The history of the wireless device's position may be used to determine a shape for the navigated passageways.

In this embodiment, the optical fiber may include multiple cores within a single cladding. Each core may be single-mode with sufficient distance and cladding separating the cores such that the light in each core does not interact significantly with the light carried in other cores. In other embodiments, the number of cores may vary, or each core may be contained in a separate optical fiber.

In some embodiments, an array of FBGs is provided within each core. Each FBG comprises a series of modulations of the core's refractive index so as to generate a spatial periodicity in the refraction index. The spacing may be chosen so that the partial reflections from each index change add coherently for a narrow band of wavelengths and therefore reflect only this narrow band of wavelengths while passing through a much broader band. During fabrication of the FBGs, the modulations are spaced by a known distance, thereby causing reflection of a known band of wavelengths. When a strain is induced on the fiber core, however, the spacing of the modulations will change, depending on the amount of strain in the core. Alternatively, backscatter or other optical phenomena that vary with bending of the optical fiber can be used to determine strain within each core.

Thus, to measure strain, light is sent down the fiber, and characteristics of the returning light are measured. For example, FBGs produce a reflected wavelength that is a function of the strain on the fiber and its temperature. This FBG technology is commercially available from a variety of sources, such as Smart Fibres Ltd. of Bracknell, England. Use of FBG technology in position sensors for teleoperational surgery is described in U.S. Pat. No. 7,930,065 (filed Jul. 20, 2006) (disclosing "Robotic Surgery System Including Position Sensors Using Fiber Bragg Gratings"), which is incorporated by reference herein in its entirety. The optical fiber may be used to monitor the shape of at least a portion of the catheter system 202. More specifically, light passing through the optical fiber is processed to detect the shape of the catheter system 202 and to utilize that information to assist in surgical procedures. The sensor system (e.g., sensor system 108) may include an interrogation system for generating and detecting the light used for determining the shape of the catheter system 202. This information, in turn, can be used to determine other related variables, such as velocity and acceleration of the parts of a medical instrument system. The sensing may be limited only to the degrees of freedom that are actuated by the teleoperational system, or it may be applied to both passive (e.g., unactuated bending of the rigid members between joints) and active (e.g., actuated movement of the instrument) degrees of freedom.

The medical instrument system may optionally include a position sensor system 220. The position sensor system 220 may be a component of an EM sensor system with the sensor 220 including one or more conductive coils that may be subjected to an externally generated electromagnetic field. Each coil of the EM sensor system 220 then produces an induced electrical signal having characteristics that depend on the position and orientation of the coil relative to the externally generated electromagnetic field. In one embodiment, the EM sensor system may be configured and positioned to measure six degrees of freedom, e.g., three position coordinates X, Y, Z and three orientation angles indicating pitch, yaw, and roll of a base point or five degrees of freedom, e.g., three position coordinates X, Y, Z and two orientation angles indicating pitch and yaw of a base point. Further description of an EM sensor system is provided in U.S. Pat. No. 6,380,732 (filed Aug. 11, 1999) (disclosing "Six-Degree of Freedom Tracking System Having a Passive Transponder on the Object Being Tracked"), which is incorporated by reference herein in its entirety.

A tracking system 230 may include the position sensor system 220 and a shape sensor system 222 for determining the position, orientation, speed, pose, and/or shape of the distal end 218 and of one or more segments 224 along the instrument 200. The tracking system 230 may be implemented as hardware, firmware, software or a combination thereof which interact with or are otherwise executed by one or more computer processors, which may include the processors of a control system 116.

The flexible catheter body 216 includes a channel 221 sized and shaped to receive an interventional instrument 226. Interventional instruments may include, for example, image capture probes, biopsy instruments, laser ablation fibers, or other surgical, diagnostic, or therapeutic tools. Interventional tools may include end effectors having a single working member such as a scalpel, a blunt blade, an optical fiber, or an electrode. Other end effectors may include, for example, forceps, graspers, scissors, or clip appliers. Examples of electrically activated end effectors include electrosurgical electrodes, transducers, sensors, and the like. In various embodiments, the interventional tool 226 may be an image capture probe that includes a distal portion with a stereoscopic or monoscopic camera at or near the distal end 218 of the flexible catheter body 216 for capturing images (including video images) that are processed by a visualization system 231 for display. The image capture probe may include a cable coupled to the camera for transmitting the captured image data. Alternatively, the image capture instrument may be a fiber-optic bundle, such as a fiberscope, that couples to the visualization system. The image capture instrument may be single or multi-spectral, for example capturing image data in one or more of the visible, infrared, or ultraviolet spectrums.

The interventional instrument 226 may house cables, linkages, or other actuation controls (not shown) that extend between the proximal and distal ends of the instrument to controllably bend the distal end of the instrument. Steerable instruments are described in detail in U.S. Pat. No. 7,316,681 (filed on Oct. 4, 2005) (disclosing "Articulated Surgical Instrument for Performing Minimally Invasive Surgery with Enhanced Dexterity and Sensitivity") and U.S. patent application Ser. No. 12/286,644 (filed Sep. 30, 2008) (disclosing "Passive Preload and Capstan Drive for Surgical Instruments") (patented as U.S. Pat. No. 9,259,274), which are incorporated by reference herein in their entireties.

The flexible catheter body 216 may also houses cables, linkages, or other steering controls (not shown) that extend between the housing 204 and the distal end 218 to controllably bend the distal end 218 as shown, for example, by the broken dashed line depictions 219 of the distal end. Steerable catheters are described in detail in U.S. patent application Ser. No. 13/274,208 (filed Oct. 14, 2011) (disclosing "Catheter with Removable Vision Probe") (patented as U.S. Pat. No. 9,452,276), which is incorporated by reference herein in its entirety. In embodiments in which the instrument system 200 is actuated by a teleoperational assembly, the housing 204 may include drive inputs that removably couple to and receive power from motorized drive elements of the teleoperational assembly. In embodiments in which the instrument system 200 is manually operated, the housing 204 may include gripping features, manual actuators, or other components for manually controlling the motion of the instrument system. The catheter system may be steerable or, alternatively, the system may be non-steerable with no integrated mechanism for operator control of the instrument bending. Also or alternatively, one or more lumens, through which medical instruments can be deployed and used at a target surgical location, are defined in the walls of the flexible body 216.

In various embodiments, the medical instrument system 200 may include a flexible bronchial instrument, such as a bronchoscope or bronchial catheter, for use in examination, diagnosis, biopsy, or treatment of a lung. The system 200 is also suited for navigation and treatment of other tissues, via natural or surgically created connected passageways, in any of a variety of anatomical systems, including the colon, the intestines, the kidneys, the brain, the heart, the circulatory system, and the like.

The information from the tracking system 230 may be sent to a navigation system 232 where it is combined with information from the visualization system 231 and/or the preoperatively obtained models to provide the surgeon or other operator with real-time position information on the display system 110 for use in the control of the instrument 200. The control system 116 may utilize the position information as feedback for positioning the instrument 200. Various systems for using fiber optic sensors to register and display a surgical instrument with surgical images are provided in U.S. patent application Ser. No. 13/107,562, filed May 13, 2011, disclosing, "Medical System Providing Dynamic Registration of a Model of an Anatomical Structure for Image-Guided Surgery" (patented as U.S. Pat. No. 8,900,131), which is incorporated by reference herein in its entirety.

In the embodiment of FIG. 2, the instrument 200 is teleoperated within the teleoperational medical system 100. In an alternative embodiment, the teleoperational assembly 102 may be replaced by direct operator control. In the direct operation alternative, various handles and operator interfaces may be included for hand-held operation of the instrument.

In alternative embodiments, the teleoperated system may include more than one slave manipulator assembly and/or more than one master assembly. The exact number of manipulator assemblies will depend on the interventional procedure and the space constraints within the operating room, among other factors. The master assemblies may be collocated, or they may be positioned in separate locations. Multiple master assemblies allow more than one operator to control one or more slave manipulator assemblies in various combinations.

Figure 3:
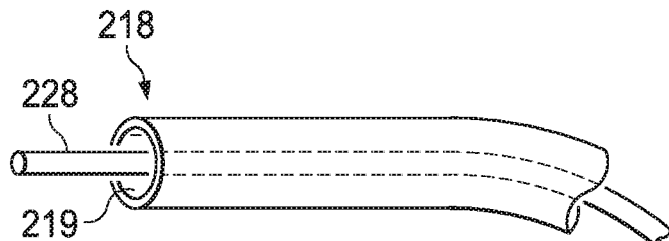
FIG. 3 illustrates a distal end of the interventional instrument system of FIG. 2 with an extended interventional tool.

As shown in greater detail in FIG. 3, interventional tool(s) 228 for such procedures as surgery, biopsy, ablation, illumination, irrigation, or suction can be deployed through the channel 221 of the flexible body 216 and used at a target location within the anatomy. The interventional tool 228 may also be the image capture probe. The tool 228 may be advanced from the opening of the channel 221 to perform the procedure and then retracted back into the channel when the procedure is complete. The interventional tool 228 may be removed from the proximal end 217 of the catheter flexible body or from another optional instrument port (not shown) along the flexible body.

In use, a clinician or the control system may select a planned deployment location within an anatomical passageway for parking a distal end of the interventional instrument to conduct the interventional procedure on a target structure. Various system and methods for planning interventional procedures and navigating to a planned deployment location are described in U.S. patent application Ser. No. 14/144,186, filed Dec. 30, 2013, disclosing, "Systems and Methods for Interventional Procedure Planning" (patented as U.S. Pat. No. 10,588,597), which is incorporated by reference herein in its entirety. Uncertainties or error values associated with the location of the target structure, with the registration of the patient model and the patient anatomy, and with the navigation of the interventional instrument impact the identification of a planned deployment location and the effectiveness of the procedure. As described below, the risk of missing the target structure due to navigational and target location uncertainty may be mitigated by representing the location of the target structure as a probabilistic target region including a collection or cloud of target points. The clinician or control system may select one or more deployment locations for parking the catheter within an anatomic passageway and then deploy the tool to engage multiple target points from the target region. By engaging multiple target points in the target region, the probability of actually engaging the target structure one or more times may be increased.

Figure 4:
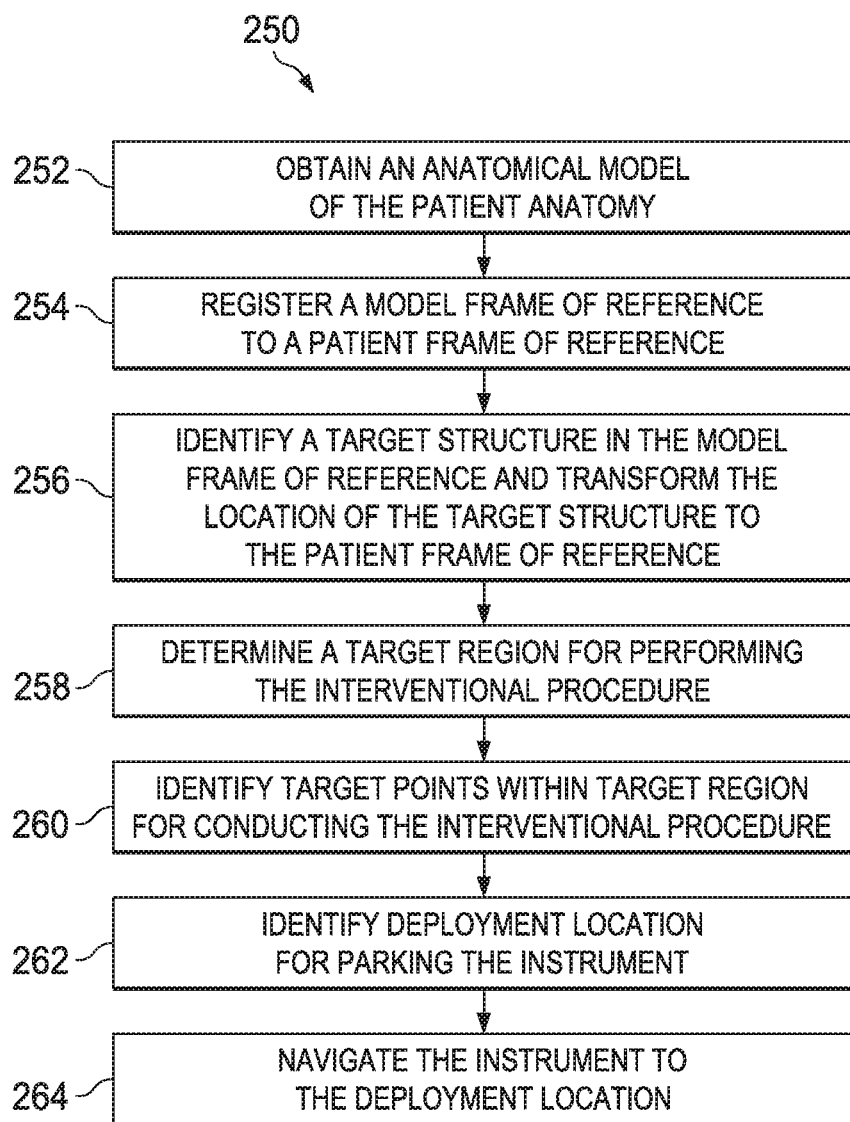
FIG. 4 is a flowchart describing a method for deploying an interventional instrument.

FIG. 4 illustrates a method 250 for identifying a procedure deployment location and navigating an interventional instrument to the deployment location. A process 252 includes obtaining an anatomical model of a patient anatomy. The anatomical model may be developed from an acquired dataset associated with the three dimensional structure of the anatomical passageways. More specifically, the model may be obtained by processing images of the interventional site recorded using imaging technology such as CT, MRI, fluoroscopy, thermography, ultrasound, OCT, DOT, thermal imaging, impedance imaging, laser imaging, nanotube X-ray imaging, or the like. Software is used to convert the recorded images into a two dimensional or three dimensional model of a partial or an entire anatomical organ or anatomical region. The model describes the various locations and shapes of the passageways and their connectivity. The images used to generate the model may be recorded preoperatively or intra-operatively during a clinical procedure. In an alternative embodiment, standard models (i.e., not patient specific) or hybrids of a standard model and patient specific data may be used. The model and any virtual images generated by the model may represent the static posture of a deformable anatomic region during one or more phases of motion (e.g., during an inspiration/expiration cycle of a lung). The model has a frame of reference and an associated model coordinate system.

Figure 5:
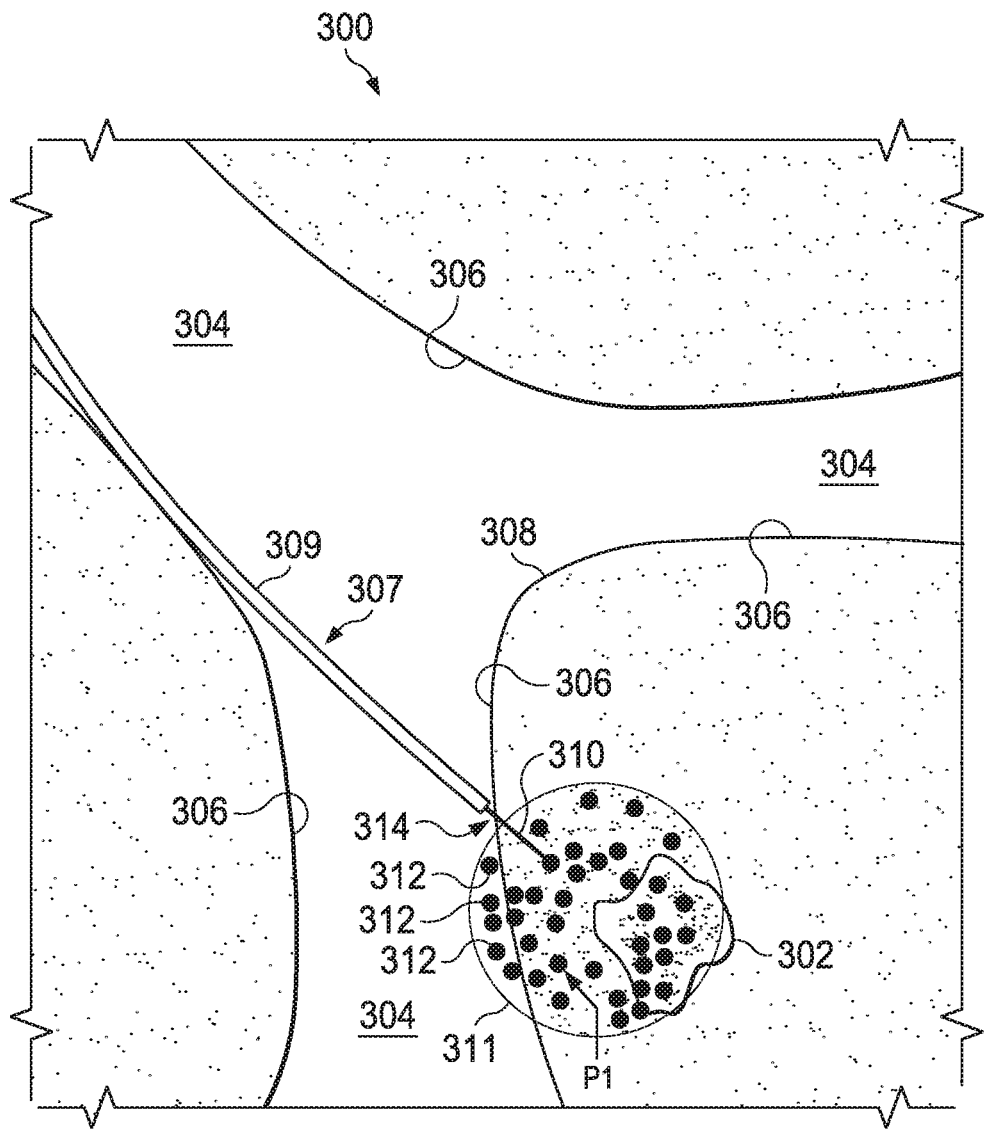
FIG. 5 illustrates an anatomical region of a patient near a target location with a distal end of an interventional instrument at a deployment location.

At a process 254, the model frame of reference is registered to a patient frame of reference so that the locations of anatomic structures identified in the model can be transformed to the patient frame of reference in which the actual patient and interventional instrument exist. Likewise, the location and orientation of the interventional instrument in the patient frame of reference can be transformed to the model frame of reference so that the movement of the instrument with respect to the modeled anatomic structures can be tracked. At a process 256, a target structure is identified in the model frame of reference and is transformed to a location in the patient frame of reference. As shown in FIG. 5, a virtual image 300 from the model depicts a target structure 302, such as a tumor, and nearby anatomic passageways 304. The passageways include passageway walls 306 and carina 308. In this embodiment, the anatomic passageways are bronchial passageways of the lung, but the systems and methods of this disclosure may be suitable for use in other natural or surgically created passageways in anatomical systems such as the colon, the intestines, the kidneys, the heart, or the circulatory system. The virtual image 300 further depicts an image of an interventional instrument 307 registered with the image of the anatomy. The interventional instrument 307 includes a flexible body 309 (substantially similar to flexible body 216) and an extended interventional tool 310. The position and orientation of the image of the interventional instrument 307 within the patient frame of reference may be determined based upon the previously described sensor systems.

A variety of error factors contribute to uncertainty about the true location of the target structure 302 relative to the instrument 307. For example, an error factor may be associated with movement of the patient after the model and patient frames of reference have been registered. As a consequence of the post-registration movement, the actual patient anatomy may no longer be in the same location or orientation predicted by the model. Another error factor may be associated with cyclical patient movement caused by, for example, patient respiration or cardiac motion. If, for example, the model is obtained from images obtained during the expiration cycle of respiration, the true location of the target structure relative to the instrument will be in a different location if the instrument is deployed during an inspiration cycle of respiration. Error factors may also be associated with errors in the sensor systems, changes in the anatomy between the time of the imaging and the time of the intervention (e.g. due to other interventional procedures or disease progression), and errors in assumptions for control algorithms used to navigate the instrument.

Referring again to FIG. 4, a process 258 includes determining a target region which represents the location of the target structure 302 with respect to the instrument as a probabilistic collection or cloud of target points. The target region may be a three dimensional area in the patient reference frame. An image of the target region 311 is shown in FIG. 5. The target region 311 is comprised of a plurality of target points 312. The distribution of target points 312 and thus the three-dimensional shape of the target region may be based upon a variety of factors, as described above. For example, the probabilistic distribution of the location of the target structure in the patient frame of reference may contribute to the point distribution. The location of the target structure within the patient frame of reference may vary due to, for example, motion between the time of pre-operative imaging and the time of the interventional procedure, cardiac motion, respiratory motion, error associated with respiration gating or sensing, and motion caused by forces applied to the anatomy by the interventional instrument. The probabilistic distribution of the pose of the distal end of the interventional instrument (catheter and/or extensible tool) in the patient frame of reference also may contribute to the target point distribution. For example, an error distribution associated with the sensor system may cause error in the instrument pose. Other contributors to the probabilistic distribution of the target structure in the patient reference frame may include motion between the time of pre-operative imaging and the time of the interventional procedure, deviations associated with assumptions made in the navigation algorithms, uncertainty and variability in the length of the interventional tool, uncertainty and variability associated with changes in orientation of the interventional tool compared to the sensed orientation of the interventional tool.

Changes to or variations in the volumetric shape of the actual target structure as compared to the pre-operative model and images may also contribute to the probabilistic distribution of the target structure in the patient reference frame.

The amount that each of these factors contributes to the probabilistic distribution of the target structure in the patient reference frame may be empirically derived by measuring or receiving information about the patient anatomy and the instrument. For example, empirical data may be obtained about the respiration motion between inspiration and expiration in pre-operative images or about the accuracy of breathing modeling and breathing holding. Empirical data may also be obtained about discrepancies between the sensed location of the instrument and the particular anatomical passageway in which the instrument is estimated to be. Statistics about the sensed location of the instrument when it is stationary (e.g., not axially advanced or rotated) across multiple respiratory or cardiac cycles may be used to determine the probabilistic distribution. Statistics about the sensed location of the instrument when subjected to different load conditions (e.g., different amounts of tension) may also be used to determine the probabilistic distribution. Empirical data about the shape of the instrument and interventional tool and the amount of bending experienced by the instrument and/or tool may be used to determine the probabilistic distribution. Empirical information may also be measured or otherwise obtained about the location of the anatomy in which the target structure is located (e.g., the firmness or elasticity of the surrounding tissue; the relative location of bones, vasculature, and connective tissue). Empirical data may also be gathered from physics-based modeling of the instrument and interventional tool to determine the amount of deformation caused on surrounding tissue. Empirical data may be measured or otherwise obtained about the physical properties of the instrument and interventional tool. Empirical data may also be derived from images of the anatomy and target structure obtained by intraoperative imaging sources such as optical visualization system, ultrasound, CT, or fluoroscopy sources.

Although the process 258 of determining a target region may involve determining a single target region comprising multiple target points, in other embodiments, more than one point cloud may be determined. For example, if an obstruction such as bone or other rigid tissue is in the region of the target structure, two target regions—one on either side of the rigid tissue—may be determined. Multiple target regions may be entirely separate or may intersect.

The target region 311 may be illustrated as a bounded volume around the theoretical locations (i.e. target points) of the target structure. Alternatively, the target region may be the collection of target points without a bounded volume around the target points. The target point cloud and/or bounded volume may be displayed as a spherical, ellipsoid, or other-shaped two- or three-dimensional volume that matches the probability distribution around the theoretical location of the target structure. The size and shape of the target region may be dependent on the properties of the specific location in the anatomy of the target structure. Different properties may apply to different parts of the anatomy. For example, the peripheral area of the lungs may experience greater movement due to cyclic anatomical motion than more central areas. Thus, the error distribution and target region size associated with a target structure in the periphery area may be larger than the distribution and target region size associated a target structure near the main bronchi. The size and shape of the target region may also take into account areas to be avoided when conducting the interventional procedure. Areas to be avoided may include areas in which conducting an interventional procedure may be dangerous to the patient or areas that may be inaccessible. Areas to avoid may include blood vessels, bone, boundaries of the lung (e.g., near the pleura or diaphragm) or sensitive organs and therefore, the presence of these anatomical features may influence the size and shape of the target region. The size and shape of the target region may also be influenced by the chance of a successful procedure. For example, a successful biopsy may be dependent upon avoiding target points with a trajectory nearly parallel to the approaching airway since such an approach would increase the risk of the interventional tool deflecting into an airway instead of puncturing the wall to obtain a biopsy. In one embodiment, a segmentation process for identifying airway passages or other structures in the anatomical images may be used to model the target structure and modify (e.g., grow) the segmented surface to account for probabilistic distribution of the location of the target structure. In other words, the size and shape of the target structure may be expanded or otherwise altered to include the probabilistic distribution of the location of the target structure.

In some embodiments, the target structure location may be divided in the sublocations, each with an associated probabilistic target region. In some embodiments, a target structure location or sublocations may be artificial locations generated to accommodate catheter motion while the biopsy instrument is being deployed or other known flexibility characteristics of the catheter or biopsy instrument. For example, if a biopsy procedure is unsuccessful due to catheter movement when using an actual target location, one or more artificial target locations may be created to compensate for the catheter movement.

Referring again to FIG. 4, a process 260 includes identifying specific target points within the target region at which to conduct the interventional procedure. For example, the specific points within the target region may be biopsy locations for sampling tissue. The selection of specific target points may be further influenced by the total number of procedures to be conducted. For example, if only two biopsies are planned within the target region, the selected target points may further apart than if six biopsies are planned at six different target points. The selection of specific target points may also be influenced by the results of prior procedures. For example, selection of the target points for a later set of biopsies in the target region may be based upon the results of an earlier biopsy. The target points may be ordered or ranked, for example, based upon probability of successful biopsy results, based upon patient safety (e.g., consider nearby fragile structures), or based upon likelihood of a satisfactory histology sample.

Referring again to FIG. 4, a process 262 includes identifying a planned catheter park location from which the interventional tool may be deployed. In one embodiment, a navigation planning module of the control system 112 identifies the planned deployment location as a location 314 along a wall of an anatomic passageway closest to or nearby to the target region or to specific target points within the target region(s). If more than one target region is identified, more than one deployment location may be determined. A different deployment location may also be identified for each target point.

Selecting the deployment location entirely on the basis of proximity to the target region may result in a selected deployment location that is inaccessible or not easily accessible by the interventional instrument. For example, the interventional instrument may be incapable of bending sufficiently within the passageway to access the proximity based deployment location. Additionally the selected deployment location or the navigational path to the deployment location may not consider anatomical constraints, such as scar or diseased tissue to avoid. As another example, a deployment location can be selected to minimize the amount of tissue deformation and thus the risk of tissue damage. Optionally, one or more deployment locations or target points may be chosen based upon the desired size of the biopsy sample. For example, a first biopsy may return a positive cytology sample based upon only a few cells. Based upon the positive cytology sample, a new target point(s) or deployment location(s) may be selected to access a larger diameter of the target structure across which to biopsy for a histology sample.

In other embodiments, a navigation planning module selects the deployment location based upon a plurality of factors, which in some instances may be procedural characteristics, such as the distance to the target region, and/or the position of the target region relative to other anatomic features. In other embodiments, the navigation planning module may additionally or alternatively receive and use information about the operational capability of the interventional instrument to determine a deployment location. For example, information pertaining to the known characteristics of the bending capability of the instrument may be considered, such as the flexibility and elasticity of the catheter material, any stiffness or preformed shape characteristics of the catheter or tools passed through the channel of the catheter, the steerability of the distal end of the catheter or tool (e.g., the degree to which the distal tip of the catheter may be curved relative to the main axis of the catheter), and the curvature along the length of the catheter. Other known characteristics of the interventional instrument may also be used to determine the deployment location including the diameter of the catheter, the diameter of the tool, the trajectory of the tool when extended from the catheter (e.g., curved, straight), the movement of the tool (e.g., sweeping, spinning, linear), the maximum angulation of the axis of the tool versus the axis of the catheter, the maximum length the tool can be extended from the catheter, and any anchoring structures at the distal tip of the catheter providing frictional contact with the passageway wall. The information pertaining to the bending capability and/or the information related to the characteristics of the interventional instrument are exemplary factors that can be used to determine the operational capability of the interventional instrument within the anatomical passageways.

The navigation planning module may also or alternatively receive and use information about the patient anatomy to determine a deployment location. Such information may include, for example, the location of the carinas of the anatomical passageways nearest to the target region and the size of the passageways nearest to the target region. Other anatomic information may include the elasticity of the anatomical passageways including the impact that any disease processes may have had on the elasticity of the passageways. The navigation planning model may also consider the surrounding anatomic tissue to, for example, select a deployment location that reduces the risk to surrounding tissue. As one example, a deployment location that causes the deployed tool to extend generally parallel to the lung wall (rather than toward it). This may minimize the risk of puncturing the lung with a deployed tool. The navigation planning model may also consider the anatomy of the target structure to access a preferred location of the target region.

For example, the deployment location may be selected such that a biopsy tool avoids a calcified part of a tumor. The shape of the target region may also be determined based upon the anatomy of the target structure so that the area of the calcified part of the tumor is identified as a low probabilistic area and would not be included in the probabilistic region.

The navigation planning module may also consider information about the relationship between the interventional instrument and the patient anatomy such as the distance of the target region or specific target points in the target region from the end of the catheter. The navigation planning module may also consider the angle of approach between the interventional tool and the passageway wall. For example, an approach angle of 90° may be impracticable due to the small size of the passageway and the bendability of the distal tip of the catheter. An approach angle of 1° may also be unsuitable because of the risk that the interventional tool may graze the surface of the passageway wall without penetrating. For these reasons, the navigation planning module may select a deployment location such that the approach angle is between approximately 30° and 90°. After the navigation planning module evaluates the factors related to the interventional instrument and the patient anatomy, a deployment location 314 on the wall of an anatomic passageway is identified.

At a process 264, the navigation planning module may provide instructions for a suggested navigational path to the planned deployment location. The clinician can then direct the distal end of the interventional instrument to the deployment location. The clinician may manually control the navigation of the interventional instrument based upon virtual or real image guidance. Alternatively, the clinician can teleoperationally control the navigation of the interventional instrument or allow computer-controlled navigation of the interventional instrument along the suggested navigational path.

Figure 6:
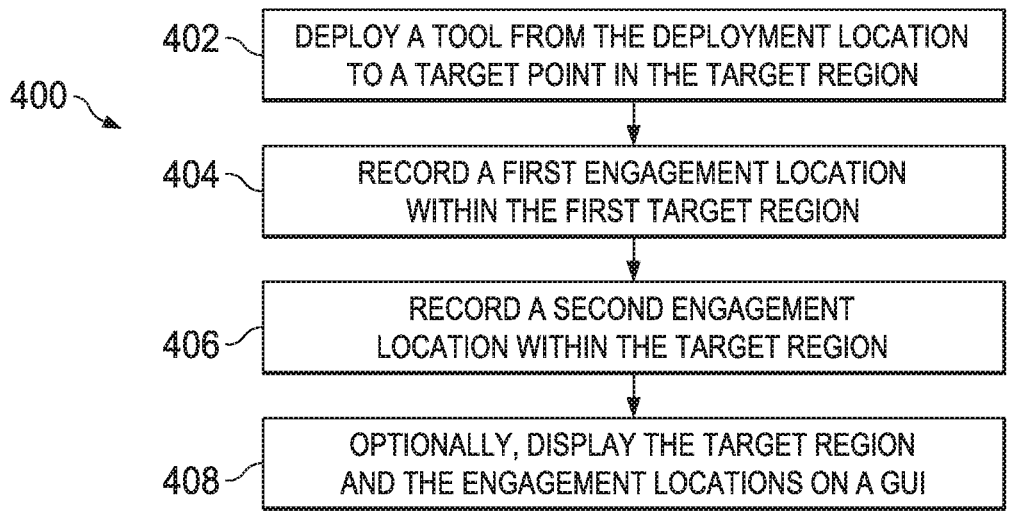
FIG. 6 is a flowchart describing a method for performing an interventional procedure.

FIG. 6 illustrates a method 400 of deploying an interventional tool from a catheter parked at a deployment location. At a process 402, an interventional tool (e.g. tool 310) is extended from the catheter parked at the deployment location toward a target point in the target region. In some circumstances, for example when a target structure is located within an anatomic passageway, the deployment location may be located within the lumen of the passageway, rather than on the wall of the passageway. The target point may be preselected by the clinician or control system. Alternatively, the target point may be any engagement point within the target region engaged by the tool when conducting the interventional procedure. At a process 404, a first engagement point within the target region may be recorded. For example, the first engagement point may be a first biopsy location. The first engagement point may be coincident with a preselected target point. Alternatively, the recorded first engagement point may be at a location different from the preselected target point. At a process 406, the interventional tool is redeployed to a second engagement point, and the second engagement point within the target region may be recorded. The redeployment of the instrument may occur from the initial deployment location. Optionally, the deployment location for parking the catheter may be changed before redeploying the instrument to the second engagement point. Optionally, the process of successive redeployments of the interventional tool may be repeated until the planned number or clinician-determined number of needed engagement procedures are completed. At an optional process 408, the target region and the engagement locations may be displayed on a graphical user interface (GUI).

Figure 7:
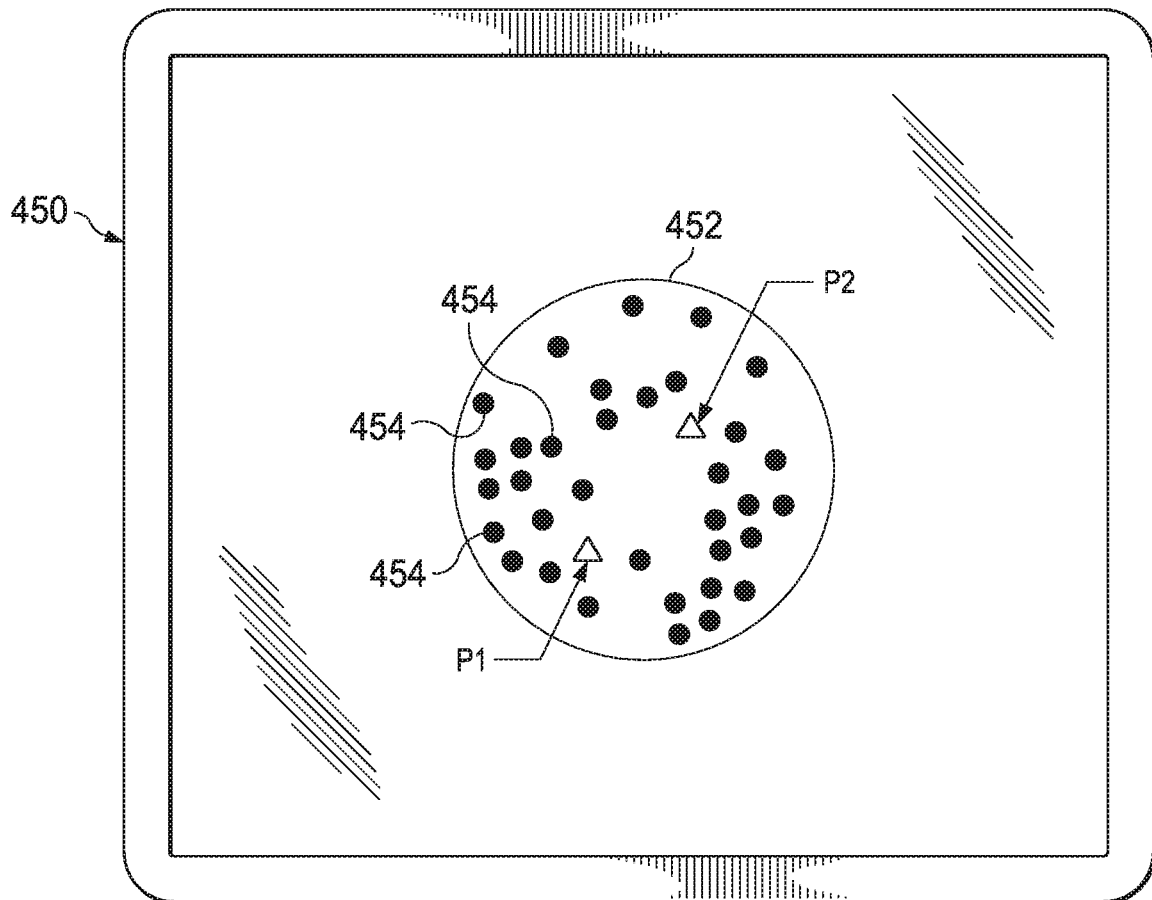
FIG. 7 is an image of a target region in the patient anatomy according to an embodiment of the disclosure.

FIG. 7 illustrates a GUI 450 for presentation on a display (e.g., display 110) depicting a target region 452 representing the probabilistic distribution of a target structure (e.g. target structure 302). The target structure includes a plurality of target points 454. A first engagement point P1 is the location of the first procedure (e.g. the first biopsy location), and a second engagement point P2 is the location of the second procedure (e.g., the second biopsy location). The engagement points P1, P2 may coincide with preselected ones of target points 454. Alternatively, the engagement points P1, P2 may be with the target region bounded volume but may not correspond to preselected target points. The engagement points may all be marked with the same symbol or each engagement point may be marked with a different symbol. If different symbols are used, each of the symbols may indicate information such as the order in which the biopsy procedures occurred or the results of the biopsy for each particular engagement point.

Figure 8:
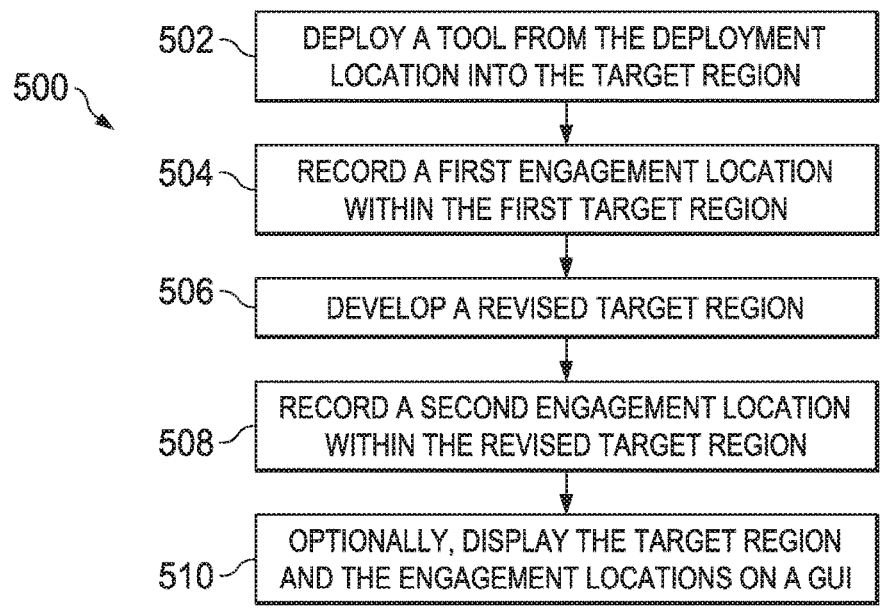
FIG. 8 is a flowchart describing a method for revising a target region.

FIG. 8 illustrates a method 500 of deploying an interventional tool from a catheter parked at a deployment location. At a process 502, an interventional tool (e.g. tool 310) is extended from the catheter parked at the deployment location toward a target point in the target region. The target point may be preselected by the clinician or control system. Alternatively, the target point may be any engagement point within the target region engaged by the tool when conducting the interventional procedure. At a process 504, a first engagement point within the target region may be recorded. For example, the first engagement point may be a first biopsy location. The first engagement point may be coincident with a preselected target point. Alternatively, the recorded first engagement point may be at a location different from the preselected target point. At a process 506, a revised target region is developed based upon the first engagement point. For example, the target region may be dynamically revised if the first engagement point was intended to coincide with a particular target point, but missed. Information from the recorded first engagement point can thus be used to better adjust the target region to the actual anatomic configuration. The revised target region may also be developed based upon the type of tissue sampled. For example, if the tissue sample from the first engagement point did not include tissue from the target structure, this information may serve as feedback to adjust the probability distribution for generating the revised target region. If no tissue was obtained due to error in the biopsy procedure, the same location may be sampled again. The revised target regions may also be developed based upon additional intra-operative imaging (e.g., optical imaging, fluoroscopic imaging) conducted during the biopsy procedure at the first engagement point. At a process 508, the interventional tool is redeployed to a second engagement point within the revised target region, and the second engagement point within the revised target region may be recorded. The redeployment of the instrument may occur from the initial deployment location. Optionally, processes 506 and 508 may be repeated until the planned number or clinician-determined number of needed engagement procedures are completed. Optionally, the deployment location for parking the catheter may be changed before redeploying the instrument to the second engagement point. At an optional process 510, the dynamically adjusting target regions and the engagement locations may be displayed on a graphical user interface (GUI).

Figure 9:
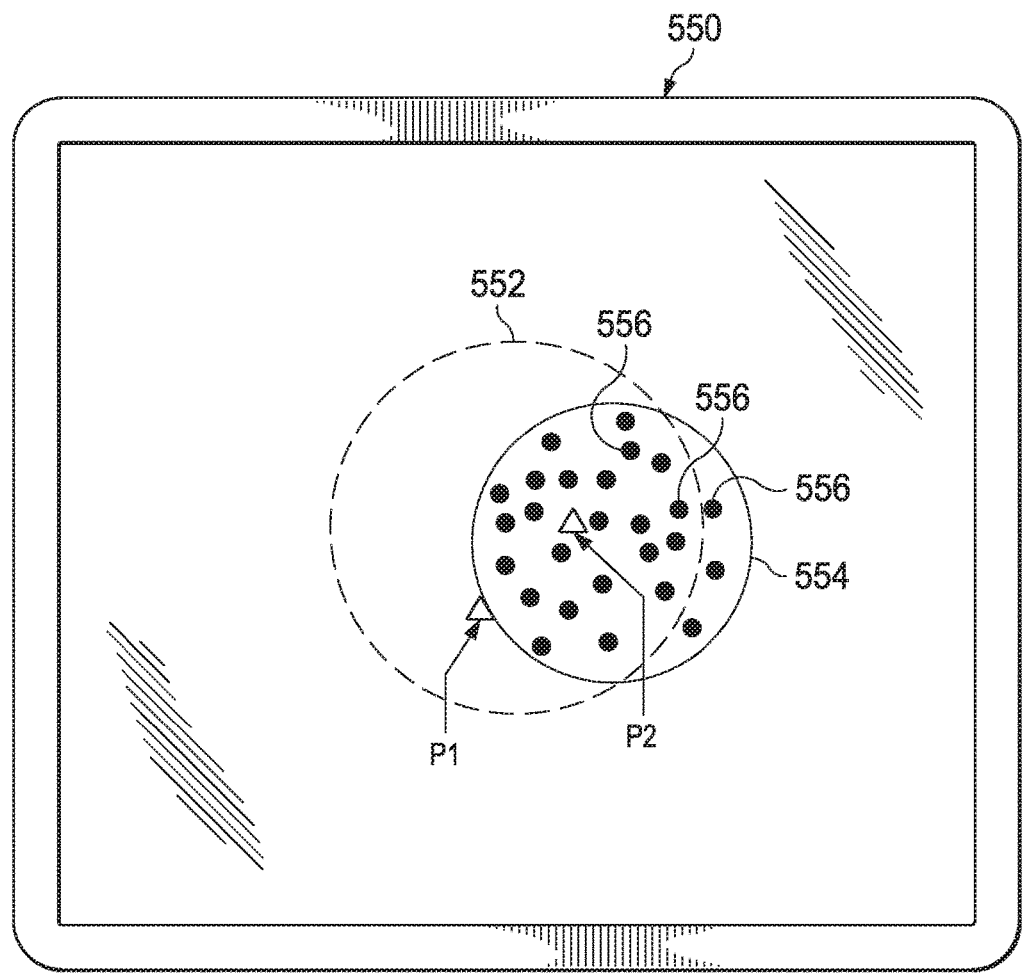
FIG. 9 is an image of a modified target region in the patient anatomy.

FIG. 9 generally illustrates the method of FIG. 8. FIG. 9 illustrates a GUI 550 for presentation on a display (e.g., display 110) depicting an initial target region 552 representing the initial probabilistic distribution of a target structure (e.g. target structure 302). A first engagement point P1 is the location of the first procedure (e.g. the first biopsy location). Based upon information gathered during the procedure (e.g. a biopsy) at engagement point P1, a revised target region 554 and revised target points 556 are determined. A second engagement point P2 is the location of the second procedure (e.g., the second biopsy location) taken in the revised target region. The engagement points P1, P2 may coincide with preselected target points in the initial or any of the revised target regions. Alternatively, the engagement points P1, P2 may be with the target region bounded volumes but may not correspond to a preselected target point. The engagement points may all be marked with the same symbol or each engagement point may be marked with a different symbol. If different symbols are used, each of the symbols may indicate information such as which target region was used to perform the procedure, the order in which the biopsy procedures occurred, or the results of the biopsy for each particular engagement point.

Figure 10:
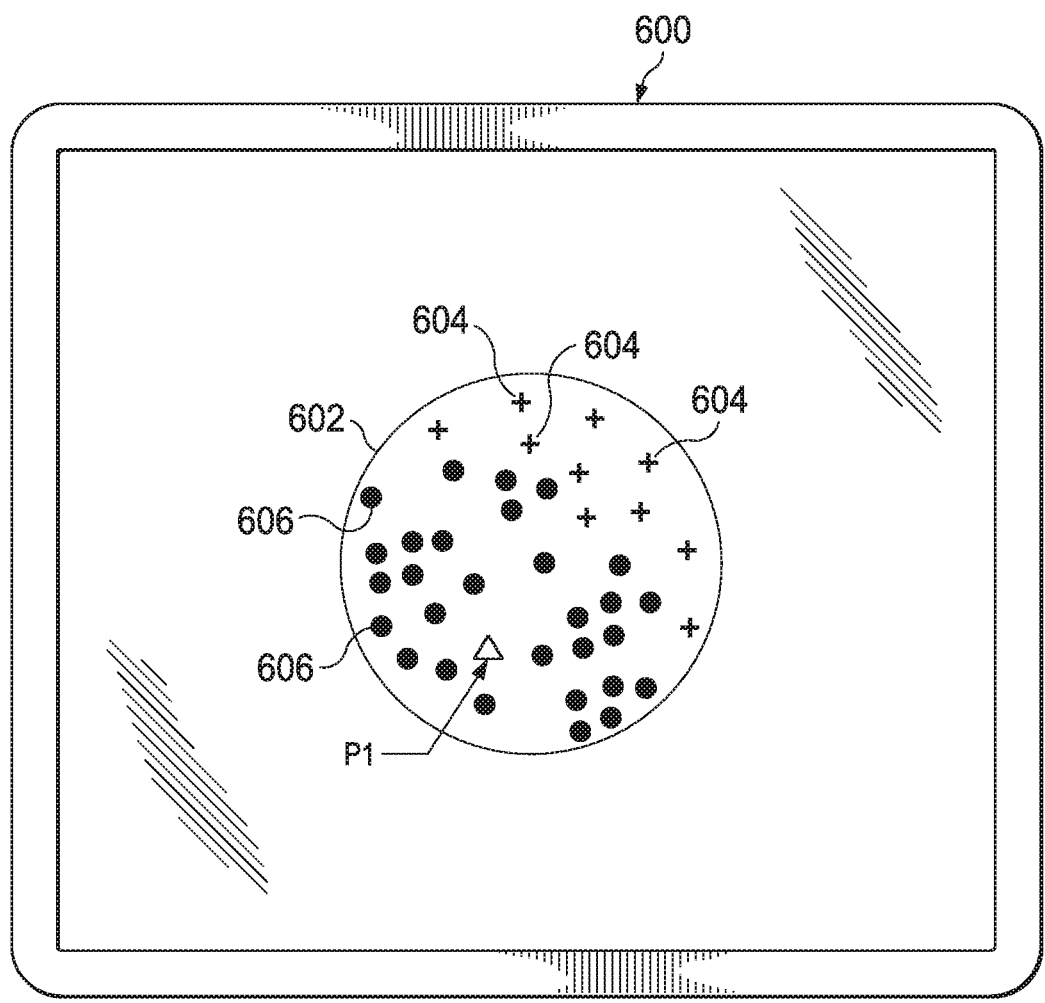
FIG. 10 is an image of a target region with coded target region markers.

The results of the methods of deploying the interventional tool may be presented or visualized in a variety of ways. For example, as shown in FIG. 10, a GUI 600 may be presented that provides coded target points that indicate target structure probability. The target points may be coded with colors, symbols, or other distinguishing markers. In this example, a target region 602 includes target points 604 having a first symbol coding and target points 606 having a second symbol coding. The coded target points 604 may indicate a different probability (e.g., higher or lower) of successful biopsy than the coded target points 606. The coded target points may also indicate where the interventional tool has previously sampled and whether the sample successfully collected target structure tissue. The coding may change dynamically based upon the results from each engagement. Target point coding may also be used to display a measure of the respiratory phase relative to a reference phase for a gated biopsy. For example, the color of the target points may change when the state of respiration is different from the gated biopsy phase.

Figure 11:
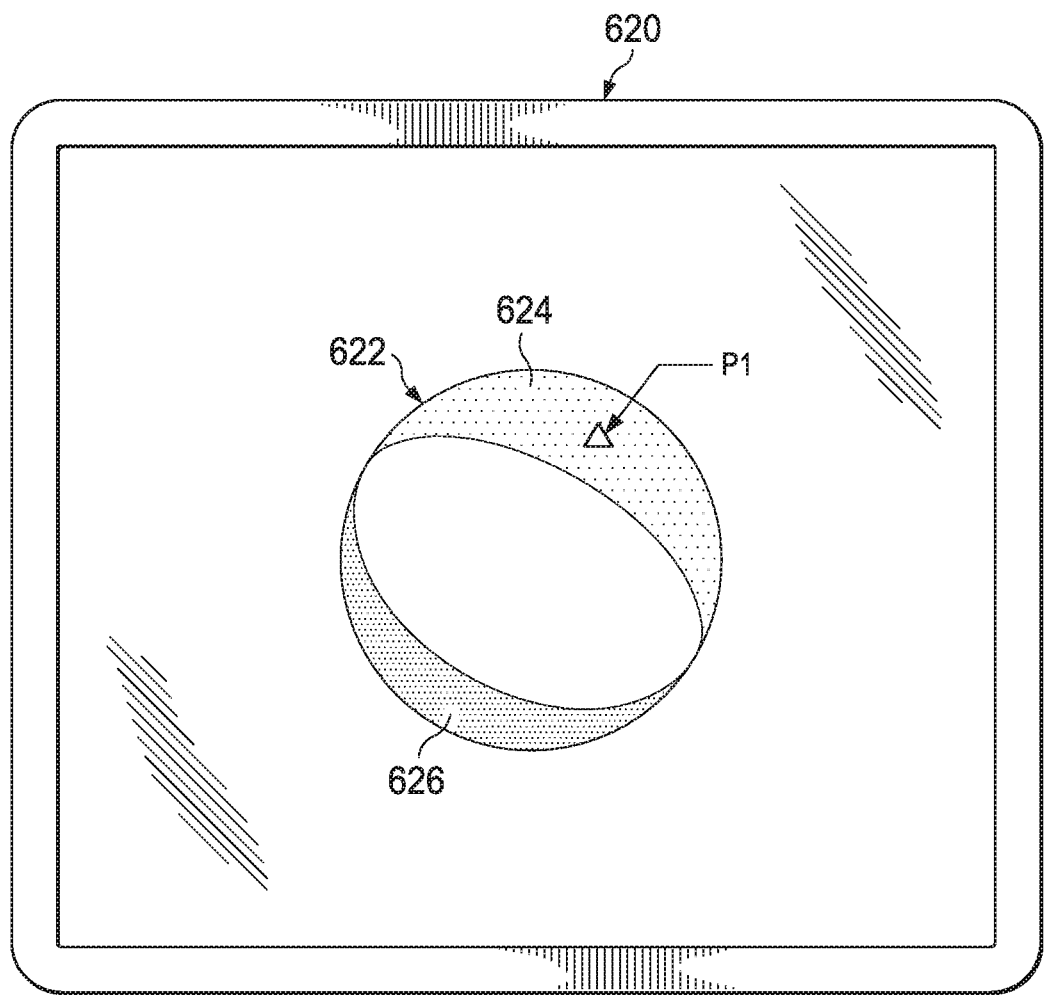
FIGS. 11 and 12 are images of a target region in the patient anatomy according to other embodiments of the disclosure.

FIG. 11 illustrates a GUI 620 that illustrates a target region 622 with region indicators 624, 626. Region 624 may indicate where successful biopsies have been performed. Region 626 may indicate where unsuccessful biopsies have been performed. The region markings may change dynamically based upon the results from each engagement.

Figure 12:
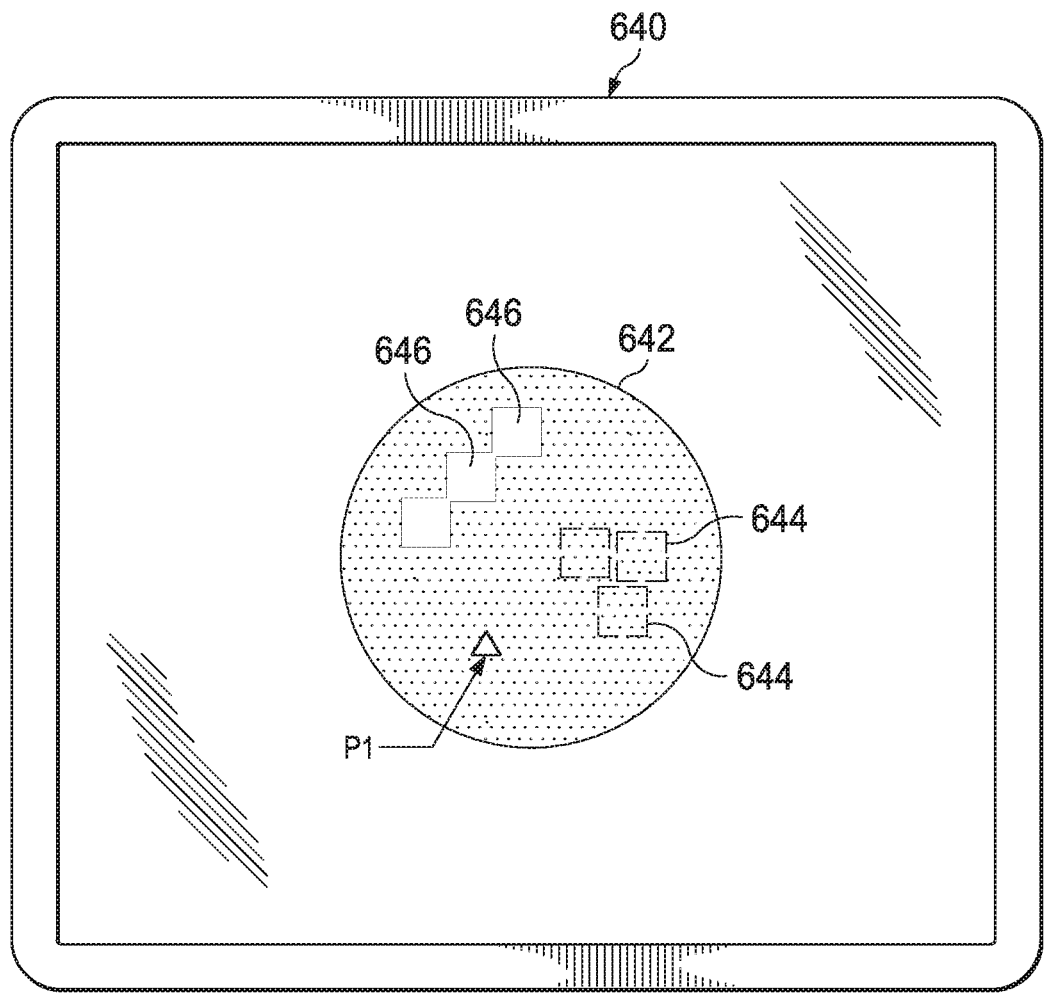

FIG. 12 illustrates a GUI 640 that illustrates a target region 642 comprised of a plurality of voxels. As engagement points corresponding to voxels are engaged (e.g., biopsied), the information obtained may allow the target region to be sculpted into a shape approximating the actual target structure. For example, voxels 646 are erased from the target region 642 to indicate that the location has been visited and the results were unsuccessful (i.e., target structure not engaged). Voxels 644 are marked in the target region 642 to indicate that the location has been visited and the results were successful (i.e., target structure engaged). In an alternative embodiment, the actual size and shape of the tissue biopsied may be displayed based on clinician input, preoperative segmentation, or intra-operative segmentation.

The results of a series of multiple interventional engagements may be stored and displayed for subsequent interventional procedures on the same target structure or area of the anatomy.

Although the systems and methods of this disclosure have been described for use in the connected bronchial passageways of the lung, they are also suited for navigation and treatment of other tissues, via natural or surgically created connected passageways, in any of a variety of anatomical systems including the colon, the intestines, the kidneys, the brain, the heart, the circulatory system, or the like. The methods and embodiments of this disclosure are also suitable for non-interventional applications.

One or more elements in embodiments of the invention may be implemented in software to execute on a processor of a computer system such as control system 112. When implemented in software, the elements of the embodiments of the invention are essentially the code segments to perform the necessary tasks. The program or code segments can be stored in a processor readable storage medium or device that may have been downloaded by way of a computer data signal embodied in a carrier wave over a transmission medium or a communication link. The processor readable storage device may include any medium that can store information including an optical medium, semiconductor medium, and magnetic medium. Processor readable storage device examples include an electronic circuit; a semiconductor device, a semiconductor memory device, a read only memory (ROM), a flash memory, an erasable programmable read only memory (EPROM); a floppy diskette, a CD-ROM, an optical disk, a hard disk, or other storage device. The code segments may be downloaded via computer networks such as the Internet, Intranet, etc.

Note that the processes and displays presented may not inherently be related to any particular computer or other apparatus. The required structure for a variety of these systems will appear as elements in the claims. In addition, the embodiments of the invention are not described with reference to any particular programming language. It will be appreciated that a variety of programming languages may be used to implement the teachings of the invention as described herein.

While certain exemplary embodiments of the invention have been described and shown in the accompanying drawings, it is to be understood that such embodiments are merely illustrative of and not restrictive on the broad invention, and that the embodiments of the invention not be limited to the specific constructions and arrangements shown and described, since various other modifications may occur to those ordinarily skilled in the art.

What is claimed is:

1. A system comprising:
an interventional instrument; and
a control system configured to:
  generate a graphical user interface (GUI) including an image of a target region for deploying the interventional instrument, wherein the target region includes a plurality of target points and is determined by a probabilistic collection of the plurality of target points, wherein a size of the target region is based at least in part on a location of a target structure within a patient anatomy;
  responsive to an engagement of the interventional instrument with tissue in the target region, update the GUI to include an engagement location marker; and
  responsive to the engagement of the interventional instrument, update the GUI to include an image of a revised target region.

2. The system of claim 1, wherein the control system is further configured to: determine the target region based on a probabilistic distribution of the target structure for performing an interventional procedure.

3. The system of claim 2 wherein the probabilistic distribution of the target structure is derived from cyclic anatomical motion data.

4. The system of claim 2 wherein the probabilistic distribution of the target structure is derived from an error distribution for a current location of the interventional instrument.

5. The system of claim 2 wherein the probabilistic distribution of the target structure is derived from an error distribution for a location of the target structure.

6. The system of claim 2 wherein the probabilistic distribution of the target structure is derived from an error distribution for a shape of the target structure.

7. The system of claim 2 wherein the probabilistic distribution of the target structure is derived from information about anatomical structures in a vicinity of the target region.

8. The system of claim 2 wherein the probabilistic distribution of the target structure is derived from information about a set of engagement characteristics of the interventional instrument.

9. The system of claim 1 wherein the engagement location marker includes information about a tissue sample from the engagement of the interventional instrument.

10. The system of claim 1 wherein the control system is further configured to:
receive image data from an imaging instrument; and
responsive to receiving the image data, update the GUI to include an image of a second revised target region.

11. A method for performing an interventional procedure, the method comprising:
generating a graphical user interface (GUI) including an image of a target region for deploying an interventional instrument, wherein the target region includes a plurality of target points and is determined by a probabilistic collection of the plurality of target points, wherein a size of the target region is based at least in part on a location of a target structure within a patient anatomy;
responsive to an engagement of the interventional instrument with tissue in the target region, updating the GUI to include an engagement location marker; and
responsive to the engagement of the interventional instrument, updating the GUI to include an image of a revised target region.

12. The method of claim 11, further comprising:
determining the target region based on a probabilistic distribution of the target structure for performing the interventional procedure.

13. The method of claim 12 wherein the probabilistic distribution of the target structure is derived from cyclic anatomical motion data.

14. The method of claim 12 wherein the probabilistic distribution of the target structure is derived from an error distribution for a current location of the interventional instrument.

15. The method of claim 12 wherein the probabilistic distribution of the target structure is derived from an error distribution for a location of the target structure.

16. The method of claim 12 wherein the probabilistic distribution of the target structure is derived from an error distribution for a shape of the target structure.

17. The method of claim 12 wherein the probabilistic distribution of the target structure is derived from information about anatomical structures in a vicinity of the target region.

18. The method of claim 12 wherein the probabilistic distribution of the target structure is derived from information about a set of engagement characteristics of the interventional instrument.

19. The method of claim 11 wherein the engagement location marker includes information about a tissue sample from the engagement of the interventional instrument.

20. The method of claim 11 further comprising:
receiving image data from an imaging instrument; and
responsive to receiving the image data, updating the GUI to include an image of a second revised target region.

* * * * *